United States Patent [19]
Sekito et al.

[11] Patent Number: 5,736,655
[45] Date of Patent: Apr. 7, 1998

[54] METHOD FOR EVALUATING A REMAINING LIFE OF A ROTATING MACHINE COIL

[75] Inventors: Shinobu Sekito; Yukio Kanazawa, both of Yokohama; Norikazu Arima, Sagamihara; Hiromichi Ito, Tokyo; Susumu Nagano, Yokohama; Makoto Tari, Kawasaki; Takeshi Tanii, Yokosuka, all of Japan

[73] Assignee: Kabushiki Kaisha Toshiba, Kawasaki, Japan

[21] Appl. No.: 660,591

[22] Filed: Jun. 11, 1996

[30] Foreign Application Priority Data

Jul. 14, 1995 [JP] Japan ................... 7-178992
Jan. 29, 1996 [JP] Japan ................... 8-012715

[51] Int. Cl.⁶ ........................... H02H 7/08
[52] U.S. Cl. .................... 73/865.9; 324/551; 324/546
[58] Field of Search ............. 73/865.9; 324/772, 324/545–547, 551

[56] References Cited

U.S. PATENT DOCUMENTS

4,525,763  6/1985  Hardy et al. ................ 324/772
4,749,894  6/1988  Iwata et al. .
5,019,760  5/1991  Chu et al. ................... 324/772
5,241,184  8/1993  Menzel .

*Primary Examiner*—Robert Raevis
*Attorney, Agent, or Firm*—Oblon, Spivak, McClelland, Maier & Neustadt, P.C.

[57] ABSTRACT

A remaining life of a stator coil resulting from galvanic corrosion between different kinds of metals in a rotating machine adopting a water cooling system and remaining life of a stator coil's insulating layer resulting from a wet heat degeneration can be positively and integrally evaluated according to the present invention by sampling a brazing section between the stator coil clip and copper wires, cutting off the sampled brazing section in a copper wire array direction, measuring a joined section brazed with a brazing material as a copper wire direction length and finding an effective sealing length of that brazing section or sampling an insulating layer of the stator coil, finding infrared spectra of the insulating layer, comparing the infrared spectra of the insulating layer of the stator coil with infrared spectra of a healthy stator coil's insulating layer not penetrated by water, finding difference spectra of an ester group of an epoxy resin used as a bonding agent of the insulating layer and predicting a period of water penetration into the stator coil's insulating layer as a wet heat degeneration period, on the basis of the difference spectra of an ester group, with the use of a relation between the difference spectra of the ester group initially found and an aging time.

8 Claims, 5 Drawing Sheets

FIG. 1

$$F(t) = \frac{1-0.3}{n+0.4}$$

METHOD FOR EVALUATING A REMAINING LIFE OF A ROTATING MACHINE COIL

BACKGROUND OF THE INVENTION

1. Field of the Invention

The present invention relates to a method for evaluating a remaining life of a coil of a rotating machine adopting a water cooling system and, in particular, to a rotating-machine coil's remaining life evaluating method for positively evaluating a remaining life of a brazing section between a clip of a stator coil of a rotating machine and copper wires resulting from galvanic corrosion of different kinds of metals there or a remaining life of an insulating layer of a stator coil of a rotating machine.

2. Description of the Related Art

As the method for confirming a state of a brazing section, that is, a covered area joined with a brazing material, between a clip of a stator coil of a rotating machine adopting a water cooling system, such as a generator, and copper wires, there is the nondestructive testing method for externally confirming the presence or absence of a clearance in a brazing section with the use of, for example, a coil pressurizing test.

However, such a method cannot quantitatively detect a very fine clearance or space.

At a brazing section of conductive section's copper wires joined with a brazing material, the development of galvanic corrosion of the different kinds of metals occurs due to the presence of water as a cooling medium. As a result, water leaks out of the brazing stator coil and the copper wires.

However it has not been possible for this conventional method to predict a time period during which such water leaks. It is the usual practice to effect repair or maintenance at a time when water leaks. For this reason it has been difficult to make a planned preventive measure at a proper time against it.

Known as the methods for confirming the dielectric strength of an insulating layer of a generator stator coil are a nondestructive electric test and dielectric strength test which are done by applying an AC commercial frequency voltage across the copper wire unit of a stator coil and an insulating layer surface.

These methods cannot quantitatively detect the wet heat degeneration of the insulating layer of the stator coil.

Further, the copper wires of the conductive section and brazing material for joining them suffer galvanic corrosion of these different kinds of metals due to the presence of water as a cooling medium. As a result, a water leak occurs at the brazing section between the clip of the generator stator coil and the copper wires and hence the water penetrates the insulating layer of the stator coil.

In the prior art, it is not possible to predict the time period during which water leaks. It is, therefore, not possible to predict at how fast a rate the dielectric strength of the insulating layer of the stator coil drops due to the wet heat degeneration and how long afterwards the stator coil can still be used. Therefore, it is difficult to take any planned preventive measure at a suitable time as in the above-mentioned case.

As set out above, the conventional confirmation method cannot predict any limited available time period after which water leaks in the brazing section between the clip of the stator coil of a rotating machine and the copper coils resulting from galvanic corrosion between different kinds of metals.

Further, it is not possible to predict how long ago the water leaks in the brazing section between the clip of the stator coil of the rotating machine and the copper wires and how long thereafters the stator coil can still be used and to predict how soon afterwards the stator coil has to be replaced with a new one.

SUMMARY OF THE INVENTION

A first object of the present invention is to provide a method for evaluating a remaining life of a rotating-machine coil, which can positively evaluate a remaining life limit of a brazing section between the clip of a stator coil of a rotating machine adopting a water cooling system and copper wires which results from galvanic corrosion of different kinds of metals.

A second object of the present invention is to provide a method for evaluating a remaining life of a rotating-machine coil, which can positively evaluating a remaining life limit of a stator coil of a rotating machine adopting a water cooling system resulting from the wet heat degeneration of the insulating layer of the stator coil.

In order to achieve the first object of the present invention, there is provided the method for evaluating a remaining life of a rotating machine coil, comprising the steps of:

sampling at least one brazing section between a clip of a stator coil in a rotating machine adopting a water cooling system and copper wires;

cutting off the sampled brazing section in copper wire array direction; and measuring cut faces of the brazing section joined with a brazing material as copper wire array direction lengths and finding them as effective sealing lengths of the brazing section and further comprising the step of predicting the shortest effective sealing length of all clips of the rotating-machine stator coil, by statistical processing, on the basis of the effective sealing length of each cut face and predicting a remaining life of the brazing section resulting from galvanic corrosion of different kinds of metals in the brazing section on the basis of the shortest effective sealing length and initially found galvanic corrosion development rate.

In the method for evaluating the remaining life of the rotating machine coil, for example, at least 5 to 6 clips are sampled from a running rotating machine. The sampled individual clip is cut off at four places in a copper wire array direction and cut faces are polished. By doing so, the bonded states of the copper wires and corrosion holes are measured in the copper wire array direction (axial direction). And a clearance length of the copper wires not bonded and corrosion hole length are subtracted from the brazing length (constant) between the clip for sealing a leak of water and the copper wires to give a remaining portion (bonded wire-to-wire portion), a value which can be found as an effective sealing length.

Further, the shortest effective sealing lengths of all the cut faces of one clip are treated as typical values of the clip to find the shortest effective sealing lengths of all the clips sampled. They can, being plotted on the Weibull distribution paper, be regressed with a straight line. It is, therefore, possible to, through the statistical processing, predict the shortest effective sealing length of all the stator coils in one rotating machine.

By dividing the predicted shortest effective sealing length by the development rate of the galvanic corrosion of different kinds of metals which is initially found by experiments, it is possible to predict a remaining life of the rotating machine stator coil resulting from the galvanic corrosion of the different kinds of metals, that is, resulting from the leakage of water from the brazing section between the clip of the rotating machine stator coil and the copper wires.

In order to achieve the second object of the present invention there is provided a method for evaluating a remaining life of a rotating machine coil, comprising the steps of sampling an insulating layer of a stator coil of a rotating machine adopting a water cooling system;

finding infrared spectra of the insulating layer;

comparing the infrared spectra of the insulating layer of a stator coil with infrared spectra of an insulating layer of a healthy stator coil not penetrated by water and finding difference spectra of an ester group in an epoxy resin used as a bonding agent of the insulating layer; and predicting a period of water penetration into the insulating layer of the stator coil as a wet heat degeneration period, on the basis of the difference spectra of the ester group, with the use of a relation between initially found difference spectra of an ester group and an aging time and further comprising the steps of measuring a breakdown voltage of the stator coil and predicting a drop rate of a dielectric strength resulting from a wet heat degeneration of the insulating layer of the stator coil on the basis of a period of water penetration into the insulating layer of the stator coil and breakdown voltage of the stator coil.

In the method for evaluating the remaining life of the rotating machine stator coil thus arranged, the stator coil whose insulating layer appears penetrated with water is sampled and an infrared spectrum analysis is performed on those sampled insulating layer portions penetrated with water to find difference spectra of its ester group. By doing so it is possible to predict the time period over which water is penetrated into the insulating layer of the stator coil.

In this case, an insulating layer formed of the same material as that of an actual-machine's stator coil is initially subjected to a forced wet heat degeneration to find a relation between different spectra of the ester group and an aging time (wet heat degeneration time) with its temperature as a parameter. By doing so it is possible to predict a period of water penetration into the stator coil insulating layer from the difference spectra of the ester group in that stator coil insulating layer, that is, in that insulating layer penetrated with water, which is measured by the remaining life evaluation method.

Further, after predicting the time period in which water starts penetrating the insulating layer of the stator coil it is possible to find a wet heat degeneration rate (drop rate of the breakdown voltage, kV/year). By doing so, it is possible to predict the drop rate of a dielectric strength resulting from the wet heat degeneration of the stator coil insulating layer after a sampling investigation time point, that is, to predict a remaining life of the insulating layer resulting from the wet heat degeneration.

In order to achieve the above-mentioned first and second objects of the present invention, there is provided a method for evaluating a remaining life of a rotating machine coil, comprising the steps of sampling at least one brazing section between a clip of a stator coil of a rotating machine adopting a water cooling system and copper wires;

cutting off the sampled section in a copper wire array direction;

measuring a portion of the cut-off brazing portion joined with a brazing material as a copper wire array direction length and finding an effective sealing length therefrom; and predicting, by statistical processing, a shortest effective sealing length of all clips of the stator coil in one rotating machine on the basis of the effective sealing length of each cut face;

predicting a remaining life of the brazing section resulting from galvanic corrosion of different kinds of metals on the basis of the shortest effective sealing length and an initially found galvanic corrosion rate;

sampling an insulating layer of the stator coil;

finding infrared spectra of the insulating layer;

comparing the infrared spectra of the insulating layer of the stator coil with infrared spectra of an insulating layer of a healthy stator coil not penetrated by water and finding difference spectra of an ester group in an epoxy region used as a bonding agent of the insulating layer;

predicting a period of water penetration into the insulating layer of the stator coil as a wet heat degeneration period, on the basis of the difference spectra of the ester group, with the use of a relation between initially found different spectra of the ester group and an aging time;

measuring a breakdown voltage of the stator coil;

predicting a drop rate of a dielectric strength of the insulating layer of the stator coil resulting from the wet heat degeneration on the basis of the period of water penetration into the insulating layer of the stator coil and the breakdown voltage of the stator coil; and finding a remaining life of the stator coil from a time point of sampling the stator coil on the basis of both the remaining life of the brazing section between clips of the stator coil and the copper wires and the drop rate of the dielectric strength of the insulating layer of the stator coil resulting from the wet heat degeneration.

In the method for evaluating the remaining life of the rotating machine coil, the remaining life of the stator coil from the time of sampling the stator coil can be integrally predicted as a sum of both the remaining life of the brazing section resulting from the galvanic corrosion of two kinds of metals and the remaining life resulting from the wet heat degeneration of the insulating layer, taking into consideration the remaining life of the brazing section of two kinds of metals which is provided between the stator coil clip and copper wires and which is predicted by the remaining life prediction method and the drop rate of the dielectric strength resulting from the wet heat degeneration of the insulating layer of the stator coil which is predicted by the remaining life predicting method.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DETAILED DESCRIPTION OF THE PREFERRED EMBODIMENTS

The embodiments of the present invention will be explained in more detail below with reference to the accompanying drawings.

(First Embodiment)

Figure 1:
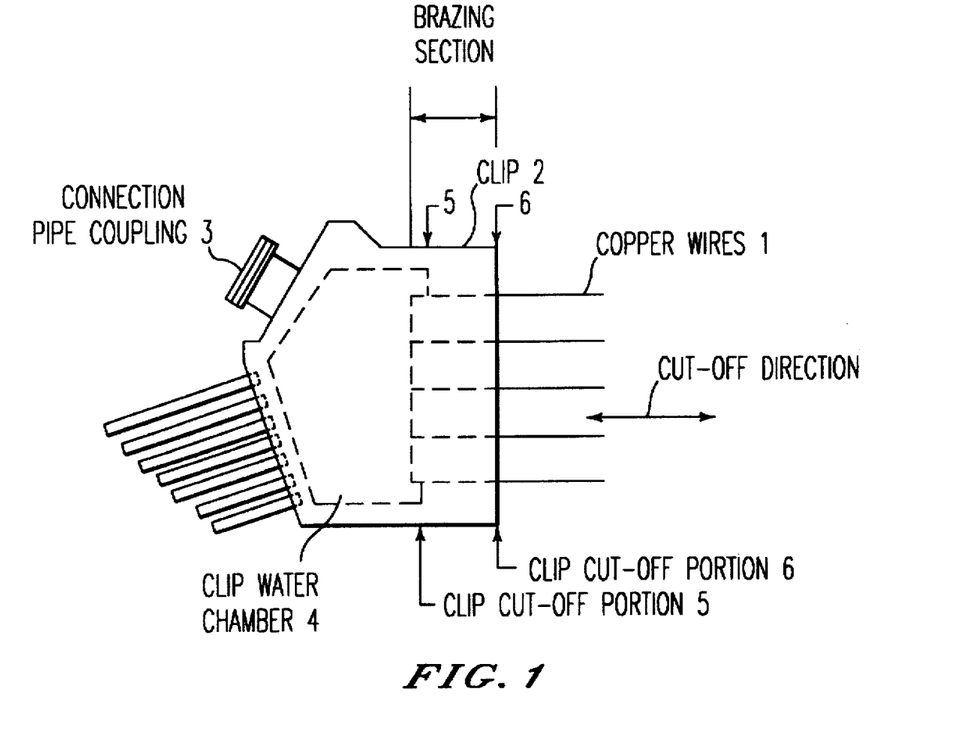
FIG. 1 is a diagrammatic view showing one example of a brazing section between a clip of a stator coil of an electric machine of a water cooling type according to the present invention.
Figure 2:
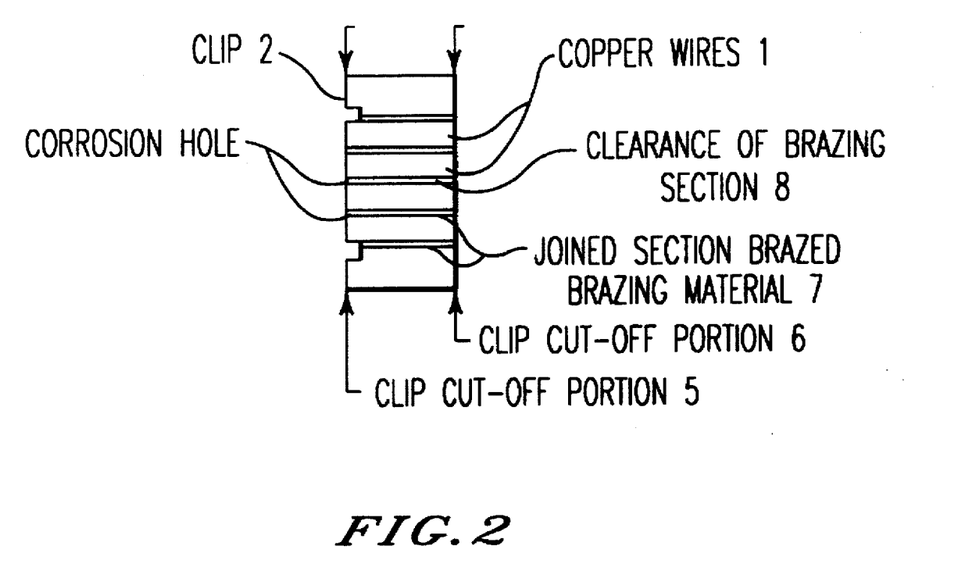
FIG. 2 is a cross-sectional view showing one example of finding a shortest sealing length by investigating a brazing section joined with copper wires and a corrosion hole developed due to galvanic corrosion of two kinds of metals.
Figure 3:
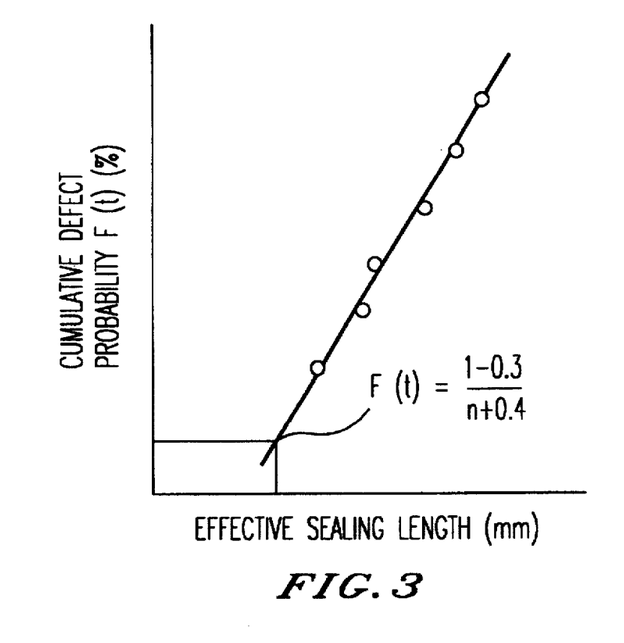
FIG. 3 is a relational graph showing one example of the procedure for predicting a shortest effective sealing length of an electric machine stator coil, with the use of the Weibull distribution paper, on the basis of those shortest sealing lengths found from individual clips sampled on the brazing section above.

FIG. 1 is a diagrammatic view showing one example of a brazing section between copper wires and clips of a stator coil of a generator adopting a water cooling system according to the present embodiment. FIG. 2 is a cross-sectional view showing one example of finding a shortest sealing length by investigating a joined state of the copper wires at the brazing section and holes developed resulting from galvanic corrosion between different kinds of metals. FIG. 3 is a relation diagram showing one example of the technique of, with the use of Weibull distribution paper, predicting a shortest effective sealing length of the generator stator coil on the basis of the shortest sealing length found from respective clips sampled at the brazing section.

The basic concept of the invention is that corrosion occurs in the brazing section at a given rate. However, since there are clearances (open areas) in the brazing material, corrosion occurs quicker because it is not necessary to corrode through the open areas. By taking several cross sectional cuts of the brazing section, it is possible to see how many openings are present and how much corrosion has already occurred. Thus, it is possible to determine how much of the brazing material remains, which is known as the "effective sealing length". Thus this section will remain sealed only until this amount of brazing is corroded away. By determining this effective sealing length, the amount of time remaining before leakage occurs can be easily determined.

In FIGS. 1 to 3, reference numeral 1 shows copper wires for the generator stator coil; 2, a clip for the generator stator coil clip; 3, a connection pipe coupling; 4, a clip water chamber; 5 and 6, clip cutoff portions; 7, a joined or brazing section; 8, clearances of the brazing section; n, the number of clips investigated or all clips in one generator; and F(t), a cumulative fault probability.

With the present embodiment, a remaining service life of the brazing section between the copper wires 1 and the clip 2 of the generator stator coil is predicted as will be set out below.

Figure 10:
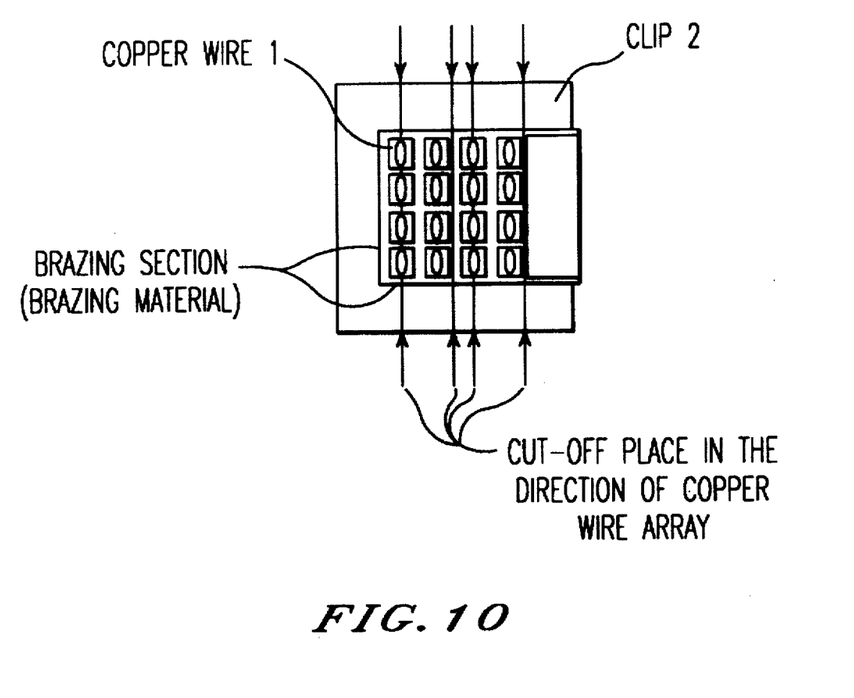
FIG. 10 is a cross sectional view looking in the axial direction of the copper wires.

First, as shown in FIG. 1, sampling is effected from the brazing section between the copper wires 1 and the clip 2 of the generator stator coil. Then the brazing section is cut off in several places (see FIG. 10) in a direction of the copper wire array and the resultant cut face is polished. Thereafter, the extent to which the brazing material is buried in the direction of the copper wires (those sections 7 joined by the brazing material between the copper wires) is predicted.

That is, at least five or sixth clips 2 are sampled from the generator now being operated and the thus sampled individual clips 2 are cut off at about four places in the copper wire array direction and their cut faces are polished. Then the joined states of the copper wires 1 and size of their corrosion holes are measured in a copper wire array direction (axis direction).

A remaining portion (a joined portion between the copper wires 1) obtained by subtracting a clearance at those unjoined copper wires plus the length of the corrosion hole from a brazing length (fixed) between the copper wires 1 and the clip 2 for water-tight sealing is measured as an effective sealing length.

In this case, the more the clip is cut off, the higher the measuring accuracy of the effective sealing length.

As shown in FIG. 3, the shortest effective sealing length on one generator is estimated by statistical processing.

That is, the shortest effective sealing length of all the cut faces of a single clip 2 is taken as a representative value of the clip 2. The shortest effective sealing length is found with respect to all the clips 2 sampled and, upon being plotted on the Weibull distribution paper, can be regressed with a straight line. From this the shortest effective sealing length of all the stator coils in one generator is estimated through the statistical processing.

Stated in more detail, as shown in FIG. 2, the cut faces of the clips are polished and measurement is made on the joined state 7 between the clip 2 and the copper wires 1, between the copper wires 1 and across the copper wire 1 in a row as well as the size of the corrosion hole resulting from galvanic corrosion between different kinds of metals. And the shortest effective sealing length of the individual clip 2 is found with the use of the calculation equation given below:

(shortest effective sealing length)=(the brazing length)−(maximum defect length)   (1)

where (maximum defect length)=the maximum value of (clearance length+corrosion hole length).

Regarding the individual clips 2, their shortest effective sealing length is found with the use of the equation (1) above and then the calculated value of the following equation is plotted on the Weibull distribution paper as shown in FIG. 3.

The cumulative defect probability $$F(t) = i/(n+1) \text{ or } (i-0.3)/(n+0.4) \quad (2)$$

where n: the number of clips 2 investigated i: out of a n number of clips examined for their effective sealing length, the number of clips below a given effective sealing length.

With respect to the sampled data (shortest sealing lengths of the individual clips) plotted on the Weibull distribution paper the regression line is drawn, as shown in FIG. 3, with the equation (2) above. The shortest effective sealing length of the generator stator coil is obtained by reading the abscissa's effective sealing length from a crosspoint between the regression line and the cumulative defect probability F(t) found by inserting n (the number of all the clips in one generator) into the equation (2).

A probable year (remaining life resulting from the galvanic corrosion), that is, a year in which water leaks from the brazing section between the copper wire 1 and the generator stator coil clip 2 due to the development of the galvanic corrosion, is predicted based on the shortest effective sealing length thus found and the galvanic corrosion development rate between different kinds of metal, that is, the rate initially found by experiments.

That is, the remaining life of the generator's brazing section resulting from the galvanic corrosion can be found, by the following calculation equation (3), based on the above-mentioned shortest effective sealing length and the galvanic corrosion development rate (mm/year) initially found by experiment.

(remaining life of the brazing section)=(shortest effective sealing lengths of all the clips 2 in the generator)/(galvanic corrosion development rate) (mm/year)  (3)

According to the present embodiment, as set out above, upon the prediction of the state of the brazing section between the generator coil clips 2 in the generator adopting a water cooling system and the copper wires 1 as well as the corrosion development state of the corrosion hole, the clip-to-copper wire-brazing sections are sampled, those sections 7 joined with the brazing material are measured as the copper wire direction lengths to find effective sealing lengths of the brazing sections (joined sections), the shortest effective sealing lengths of all the stator coil clips 2 in one generator are predicted by the statistical processing on the basis of the effective sealing lengths of the respective cut faces, that is, by regressing, with a specific straight line, a relation between the shortest effective sealing lengths of the respective clips 2 and the cumulative defect probability and the remaining life of the brazing section resulting from the galvanic corrosion is predicted based on the shortest effective lengths and initially found galvanic corrosion development rate, in actual practice, by dividing the shortest effective sealing length by the galvanic corrosion development rate.

By finding the effective sealing lengths of the brazing sections between the copper wires 1 and the stator coil clips 2 in the generator adopting the water cooling system it is possible to predict the shortest effective sealing lengths of all the brazing sections and positively predict and evaluate the remaining life of the brazing section resulting from the galvanic corrosion.

By doing so, it is possible to evaluate the remaining life of the brazing section (joined section) for water leakage so that there arises no leakage of water as a cooling medium.

Further, a planned protective measure can also be properly made through the prediction of the remaining life resulting from the galvanic corrosion. By preventing an unexpected failure, such as a machine stop, it is possible to supply stable power and expect a lowering in the cost of maintenance.

(Second Embodiment)

Figure 4:
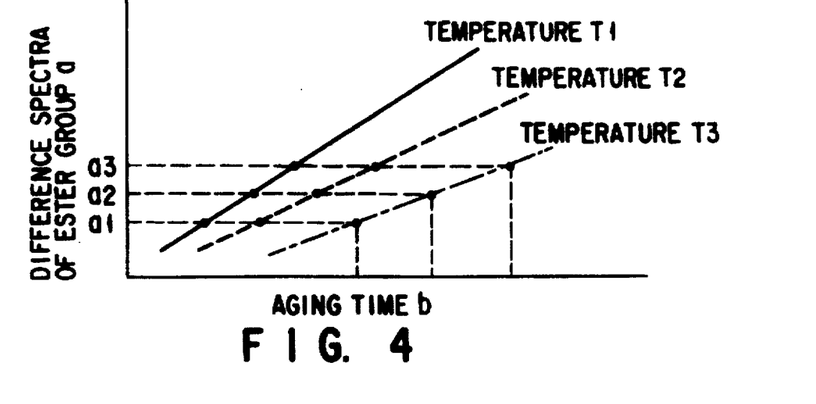
FIG. 4 is a characteristic curve showing one example of a relation between difference spectra of an ester group resulting from the wet heat degeneration of an insulating layer of the stator coil of an electrical machine of a water cooling system according to the present invention.
Figure 5:
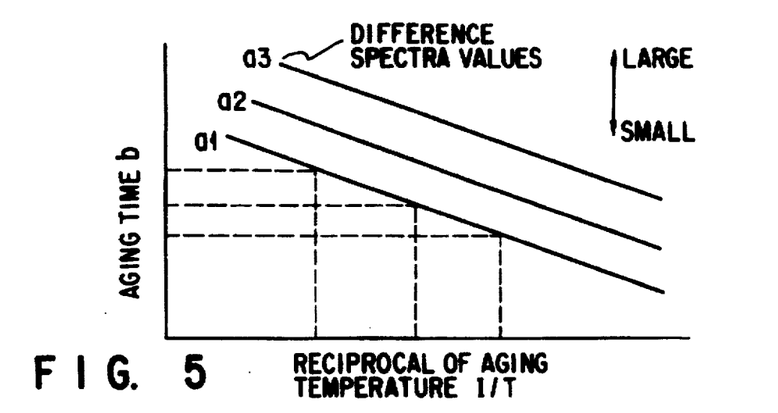
FIG. 5 is a characteristic curve showing one example of a relation between an aging time (wet heat degeneration time) and an aging temperature with the difference spectra of the ester group (FIG. 4) as a parameter.
Figure 6:
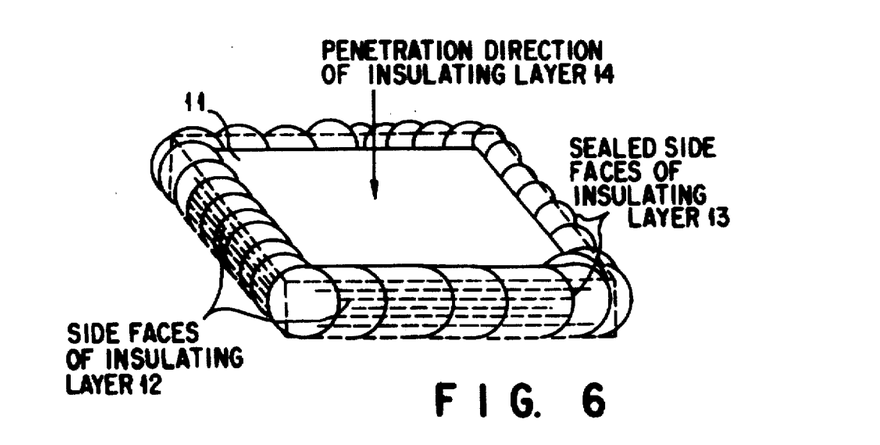
FIG. 6 is a conceptual diagram showing one example of an insulating sample prepared on a wet heat degeneration experiment where, out of sixth faces of the sample with a water penetration path test in an actual-machine stator core, the remaining five faces are sealed.
Figure 7:
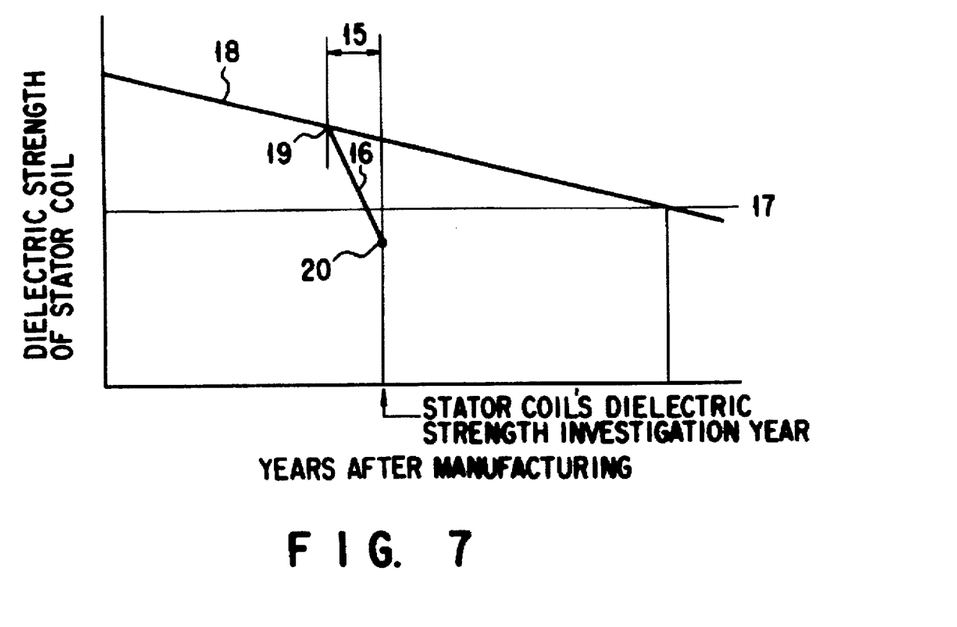
FIG. 7 is a graph showing one example of, from a drop line of a dielectric strength by the usual aging as well as from a breakdown voltage and wet heat degeneration period of the actual-machine stator coil resulting from the wet heat degeneration, finding a drop rate of the dielectric strength by the wet heat degeneration.
Figure 8:
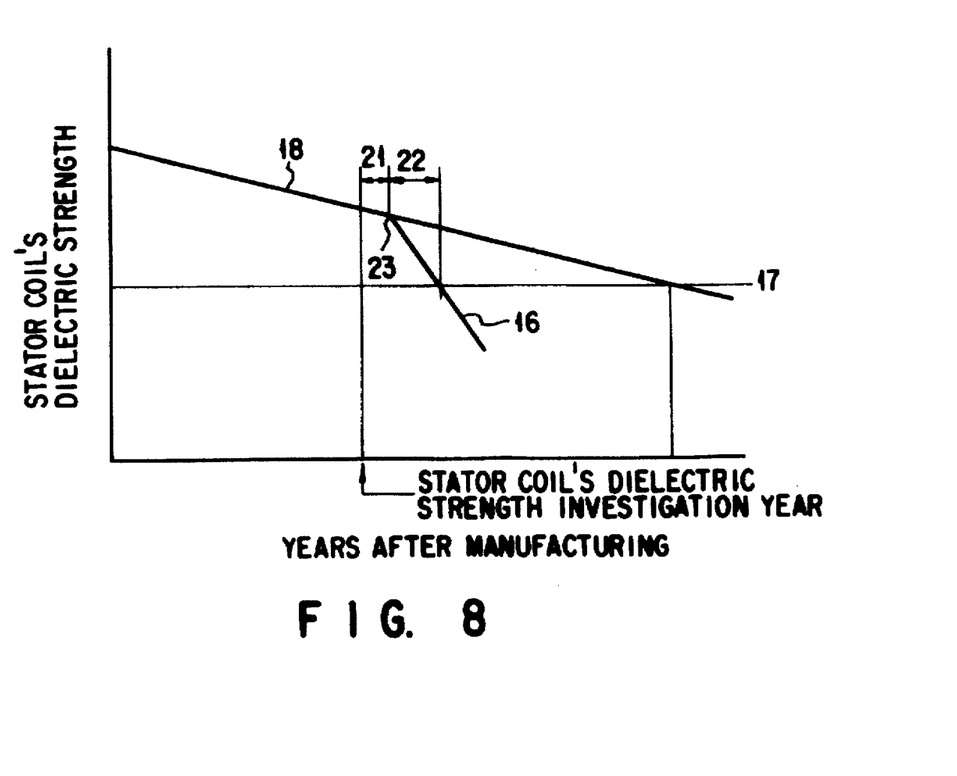
FIG. 8 is a graph showing one example of predicting an overall remaining life of the stator coil, taking into consideration both the drop rate of the dielectric strength resulting from the wet heat degeneration of the insulating layer of the stator coil and the remaining life resulting from galvanic corrosion of two kinds of metals which is developed between the stator coil clip and copper wires.
Figure 9:
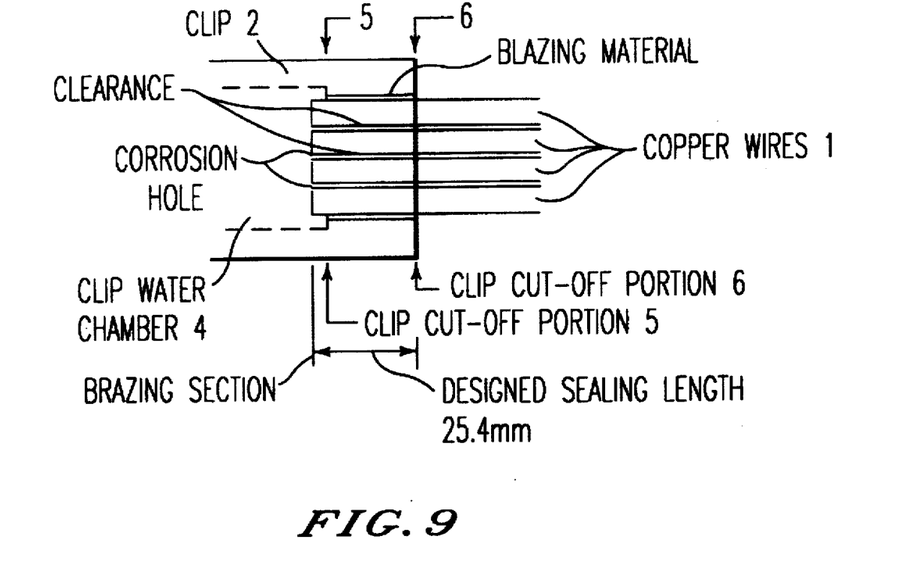
FIG. 9 is a cross sectional view similar to FIG. 2 which shows a detail of the brazing material.

FIG. 4 is a graph showing a characteristic curve of one example representing a relation between an aging (water penetration) time, that is, the time at which an epoxy resin as a bonding agent for an insulating layer is wet heat aged through the water penetration into the insulating layer of a stator coil in a generator adopting a water cooling system in accordance with the present embodiment, and difference spectra of an ester group in the epoxy resin. FIG. 5 shows one example representing a relation between the aging time of the insulating layer and the temperature with the difference spectra of the ester group as a parameter on the basis of a graph of FIG. 4. FIG. 6 is a concept diagram showing one example of a specimen insulating layer block of an experimentally aged stator coil with its five faces sealed for finding the relations shown in FIGS. 4 and 5. FIG. 7 is a graph showing one procedure for predicting, based on the different spectra of an ester group in an insulating layer of a water-penetrated practical stator coil, a water penetration time (wet heat degeneration time) with the use of the relation of the difference spectra of the experimentally found ester group to the aging time and finding a drop rate in the dielectric strength of the wet heat degenerated stator coil from a breakdown voltage of the water-penetrated stator core and usual aged wires. FIG. 8 is a graph showing one example of a procedure for integrally predicting a stator coil's remaining life from both the remaining life of the stator core clip-to-copper wire brazing section (brazing section resulting from the galvanic corrosion between different kinds of metals) obtained by the remaining life evaluation method corresponding to the first embodiment through the sampling of a stator coil with its insulating layer not yet penetrated with water and the remaining life of a stator core clip-to-copper wire brazing section resulting from the wet heat degeneration in which case water is penetrated into an insulating layer in the stator coil.

It is to be noted that, in FIGS. 4 to 8, $a_1$, $a_2$, $a_3$ represent difference spectra of the ester group after the insulating layer of the stator coil has been wet heat degenerated with the aging time b.

Further, reference numeral 11 shows one penetration-direction face of the insulating layer aged; 12, the side faces of the insulating layer and 14; the penetration direction of the insulating layer.

Reference numeral 15 shows the period (wet heat degeneration period) in which water penetrates the insulting layer; 16, a drop line of the dielectric strength of the stator coil resulting from the wet heat degeneration of the insulating layer; 17, a line (life line) for the dielectric strength necessary for a stable operation; 18, an aging line for the dielectric strength of an ordinary stator coil; 19, the dielectric strength when water starts penetrating the insulating layer resulting from an ordinary aging; 20, the breakdown voltage of the stator coil whose insulating layer is water-penetrated; 21, a remaining life of the clip-to-copper wire brazing section resulting from the galvanic corrosion; 22, a remaining life of the stator core resulting from the wet heat degeneration; and 23, the dielectric strength of the stator coil when water starts penetrating the insulating layer due to the formation of a leak path in the clip-to-copper wire brazing section.

With the present embodiment, the remaining life of the generator stator coil is predicted as will be set out below.

As shown in FIG. 6, except one penetration-direction 14 face only, the insulating layer is sealed on five faces, that is, the four side faces 12 and penetration-direction 14 bottom face, and aged in pure water at a temperature close to an operation temperature. During a portion of the aging, the insulating layer is sampled, followed by the infrared spectral analysis of an epoxy resin being a bonding agent of the insulating layer. By doing so, the relation between the difference spectra of the ester group and the aging time as shown in FIGS. 4 and 5 is found.

Then the actual-machine stator coil whose insulating layer is water-penetrated is sampled and the infrared spectrum analysis is performed and measurement is made of the difference spectra a of the ester group. Thereafter, the aging time (wet heat degeneration period) b is found from FIG. 4 or FIG. 5.

Then a commercial frequency voltage is applied to the copper wires 1 of the stator coil and, with the insulating surface of a linear section (corresponding to the stator core slot section) as a ground electrode, measurement is made of a breakdown voltage 20 of the actual stator coil.

In this case, the relation between the breakdown voltage 20 of the above-mentioned actual-machine stator coil and the wet heat degeneration period 15 can be shown on the aging line 18 of the dielectric strength of the stator coil as in FIG. 7.

That is, from FIG. 7 it is found that, through the penetration of the water into the insulating layer of the stator coil, the breakdown voltage of the stator coil is dropped, during the wet heat degeneration period, from the line 19–20 in the case of the usual aging.

Thus the drop rate of the dielectric strength over the wet heat degeneration time 15 can be found from the following equation (4).

(drop rate of the dielectric strength resulting from the wet heat degeneration)=(breakdown voltage 19 at a wet heat degeneration start time)−(breakdown voltage 20 after the wet heat degeneration)/(wet heat degeneration period 15)   (4)

Then a remaining life 21 of the brazing section between the stator coil clips and the copper wires 1 resulting from the galvanic corrosion is found, through sampling investigation of the actual-machine stator coils, as in the case of the remaining life evaluation method of the first embodiment.

With a point 23 on the usual aging line as a starting point in FIG. 8 a drop line 16 for the dielectric strength of the stator coil resulting from the wet heat degeneration is drawn with the use of the drop rate of the dielectric strength resulting from the wet heat generation found from the equation (4) above. From a crosspoint between the drop line 16 and the dielectric strength line 17 necessary for safe operation it is possible to predict the remaining life 22 of the stator core resulting from the wet heat degeneration in the case where water penetrates the insulating layer of the stator coil.

That is, the remaining life of the stator coil of the generator adopting the water cooling system can be predicted from the following equation (5).

(remaining life of a water cooling system stator coil)=(remaining life 21 of the brazing section between the clips of the stator coil and the copper wires)+(remaining life 22 of the stator coil resulting from the wet heat degeneration)   (5)

With the present embodiment, as set out above, the drop line 16 of the dielectric strength 16 is found, with respect to the insulating layer of the same material as that of the stator coil of a generator adopting the water cooling system, by predicting the wet heat degeneration characteristic (relation between the difference spectra of the ester group and the aging time—FIG. 4) initially found from the experimental aging, the breakdown voltage 20 of the actual-machine stator coils whose insulating layer is water-penetrated, and the aging time (water penetration period=wet heat degeneration time) 15 resulting from the difference spectra a of the ester group. Then, in order to evaluate the remaining life with respect to the sampled stator coils, the remaining life of the coils in the generator adopting the water cooling system is predicted through the arithmetic addition of both the remaining lives 21 and 22, that is, through the addition of the prediction value of the remaining life 21 of the stator coil clip-to-copper wire brazing section resulting from the galvanic corrosion obtained by the same remaining life evaluation method as that of the first embodiment and the prediction value 22 of the remaining life 22 of the stator coil's insulating layer resulting from the wet heat degeneration through the use of the drop line (drop ratio) 16 of the dielectric strength resulting from the wet heat degeneration as found either experimentally or by the investigation into the actual-machine stator coil penetrated by the water.

Thus, the remaining life of the stator coil as a whole is integrally predicted by both the remaining life 21 of the stator coil clip-to-copper coil brazing section in the generator adopting the water cooling system and the remaining life 22 of the insulating layer of the stator coil penetrated by the water, that is, both the remaining lives 21 and 22 not understandable from a nondestructive test from a surface and an electric test.

Further, a planned protective measure can be taken at a proper time through the prediction of the above-mentioned remaining lives. By preventing occurrence of an unexpected machine fault stop and so on it is possible to supply stable electric power and expect a lowering in maintenance cost.

(Other Embodiments)

The present invention is not restricted to the above-mentioned embodiment and can be put to practical reduction.

(a) Although, in the first embodiment, the shortest effective sealing lengths of the individual clips have been explained as being used as the statistical data, the present invention is not restricted thereto. As many cut faces as practical can be made in the individual clips in a way as shown in FIG. 2. In this case, the shortest effective sealing lengths of the cut faces can be used as the statistical processing data, these lengths be plotted on the Weibull distribution paper and the shortest effective sealing lengths of all the clips in the generator be read out with the use of the equation (6) below.

(cumulative defect probability) $F(t)$ 9=$i/(n\times m+1)$ or =$(i-0.3)/(n\times m+0.4)$   (6)

Here n: the number of the clips 2 in one generator;

m: the number of cut faces investigated per clip; and i: the number of any effective sealing length or below.

(b) In the second embodiment it is possible to find the relation of difference spectra of an ester group to an aging time, as well as the drop rate of dielectric strength, by, instead of the aging of the insulating layer initially effected experimentally, forcibly creating a leak path between the clip 2 and the copper wires 1 in a plurality of stator coils of an actual machine, effecting aging in a simulated state of operation through the penetration of cooling water into the stator coil and perform a sampling investigation during a portion of the aging.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A method for evaluating a remaining life of a rotating machine coil, comprising the steps of:

obtaining effective sealing lengths on the basis of measured cut faces of brazing sections;

predicting short effective length of all clips of a rotating-machine stator coil, by statistical processing, on the basis of the effective sealing length of each cut face; and predicting a remaining life of the brazing sections resulting from galvanic corrosion of different kinds of metals on the basis of the shortest effective sealing length and initially found galvanic corrosion development rate of such metals.

2. The method according to claim 1, wherein the prediction of the shortest effective sealing length by the statistical processing is made by regressing, with a straight line, a relation between the shortest effective sealing length of each clip and a cumulative defect probability with the use of the Weibull distribution.

3. The method according to claim 1, wherein the prediction of the remaining life of the brazing section is made by dividing the shortest effective sealing length by the galvanic corrosion development rate.

4. A method for evaluating a remaining life of a rotating machine coil, comprising the step of sampling an insulating layer of a stator coil of a rotating machine adopting a water cooling system;

finding infrared spectra of the insulating layer;

comparing the infrared spectra of the insulating layer of a stator coil with infrared spectra of an insulating layer of a healthy stator coil not penetrated by water and finding difference spectra of an ester group in an epoxy resin used as a bonding agent of the insulating layer; and predicting a period of water penetration into the insulating layer of the stator coil as a wet heat degeneration period, on the basis of the difference spectra of the ester group, with the use of a relation between initially found difference spectra of an ester group and an aging time.

5. The method according to claim 4, wherein the relation between the difference spectra of the ester group and the aging time is initially found by causing the insulating layer of a specimen stator coil made of the same material as that of the stator coil to be wet heat degenerated through experimental aging in pure water with a temperature as a parameter and performing infrared spectrum analysis.

6. The method according to claim 5, wherein the experimental aging of the insulating layer in pure water is effected through such a possible path of water into the insulting layer of the stator coil that water is directly penetrated into only one water penetration face of a cut-off block-like portion of the specimen stator coil with remaining five faces thereof sealed.

7. The method according to claim 4, further comprising measuring a breakdown voltage of the stator coil; and predicting a drop rate of a dielectric strength resulting from a wet heat degeneration of the insulating layer of the stator coil on the basis of a period of water penetration into the insulating layer of the stator coil and breakdown voltage of the stator coil.

8. A method for evaluating a remaining life of a rotating machine coil, comprising the steps of:

obtaining effective sealing lengths on the basis of measured cut faces of brazing sections;

predicting, by statistical processing, a shortest effective sealing length of all clips of the stator coil in one rotating machine on the basis of the effective sealing length of each cut face;

predicting a remaining life of the brazing section resulting from a galvanic corrosion of different kinds of metals on the basis of the shortest effective sealing length and an initially found galvanic corrosion rate;

comparing infrared spectra of the insulating layer of the stator coil with infrared spectra of an insulating layer of a healthy stator coil not penetrated by water and finding difference spectra of an ester group in an epoxy resin used as a bonding agent of the insulating layer;

predicting a period of water penetration into the insulating layer of the stator coil as a wet heat degeneration period, on the basis of the difference spectra of the ester group, with the use of a relation between initially found different spectra of the ester group and aging time;

measuring a breakdown voltage of the stator coil;

predicting a drop rate of a dielectric strength of the insulating layer of the stator coil resulting from the wet heat degeneration on the basis of the period of water penetration into the insulating layer of the stator coil and the breakdown voltage of the stator coil; and finding a remaining life of the stator coil from a time point of sampling the stator coil on the basis of both the remaining life of the brazing section between clips of the stator coil and the copper wires and the drop rate of the dielectric strength of the insulating layer of the stator coil resulting from the wet heat degeneration.

* * * * *